(12) United States Patent
Strózyk et al.

(10) Patent No.: US 10,588,508 B2
(45) Date of Patent: Mar. 17, 2020

(54) OPHTHALMIC APPARATUS

(71) Applicant: CANON KABUSHIKI KAISHA, Tokyo (JP)

(72) Inventors: Pawel Strózyk, Wroclaw (PL); Slawomir Orlowski, Torun (PL); Pawel Dalasiński, Torun (PL); Maciej Pańkowiec, Torun (PL); Krzysztof Piotrowski, Wroclaw (PL); Masao Shikaumi, Tokyo (JP); Yukio Sakagawa, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 210 days.

(21) Appl. No.: 15/833,766

(22) Filed: Dec. 6, 2017

(65) Prior Publication Data
US 2018/0153401 A1    Jun. 7, 2018

(30) Foreign Application Priority Data
Dec. 7, 2016    (JP) .................................. 2016-237684

(51) Int. Cl.
*A61B 3/10*    (2006.01)
*A61B 3/02*    (2006.01)
(Continued)

(52) U.S. Cl.
CPC .............. *A61B 3/12* (2013.01); *A61B 3/0008* (2013.01); *A61B 3/0041* (2013.01);
(Continued)

(58) Field of Classification Search
CPC .............. G02B 26/101; G02B 27/0093; G02B 27/2214; G02B 27/225; G02B 26/08; G02B 26/0833; G02B 26/085; G02B 26/0875; G02B 26/10; G02B 27/0075; G02B 6/34; G02B 27/0172; G02B 6/105; G02B 6/02066; G02B 6/274; G02B 6/2766; G02B 2027/0127; G02B 2027/0134; G02B 27/2264; G02B 27/286; G02B 3/14; G02B 6/0016; G02B 6/0035; G02B 6/02; G02B 6/27; G02B 6/32; G02F 1/01; G02F 1/11; G02F 1/17; G02F 1/19; G02F 1/29;
(Continued)

(56) References Cited

U.S. PATENT DOCUMENTS

2018/0041720 A1*    2/2018    Wada ....................... H04N 3/08

FOREIGN PATENT DOCUMENTS

JP            7-178053  A        7/1995

* cited by examiner

*Primary Examiner* — Brandi N Thomas
(74) *Attorney, Agent, or Firm* — Canon U.S.A., Inc. I.P. Division

(57) ABSTRACT

An ophthalmic apparatus includes a control unit configured to control a scanning unit so that scanning lines of a first field and scanning lines of a second field are alternately arranged in a direction crossing the scanning lines, and a detection unit configured to, in a case where one of first front images of the first field is selected as a reference image, detect movement of the subject's eye using information indicating a position gap between the reference image and the first front images, and detect the movement of the subject's eye using information indicating a position gap between the reference image and second front images of the second field and information indicating a difference in position between the first field and the second field.

21 Claims, 8 Drawing Sheets

(51) Int. Cl.
  *A61B 3/12*  (2006.01)
  *A61B 3/13*  (2006.01)
  *A61B 3/00*  (2006.01)
  *A61B 5/00*  (2006.01)
  *A61B 3/117* (2006.01)
  *A61B 3/14*  (2006.01)

(52) U.S. Cl.
  CPC ............ *A61B 3/0058* (2013.01); *A61B 3/102* (2013.01); *A61B 3/1025* (2013.01); *A61B 3/117* (2013.01); *A61B 3/1225* (2013.01); *A61B 3/13* (2013.01); *A61B 3/14* (2013.01); *A61B 5/0066* (2013.01); *G06T 2207/30041* (2013.01)

(58) Field of Classification Search
  CPC .... G02F 1/33; G02F 2001/294; G02F 1/1393; G02F 1/1326; G02F 1/295
  USPC ........ 351/200, 205–206, 209–211, 221–223, 351/243–246
  See application file for complete search history.

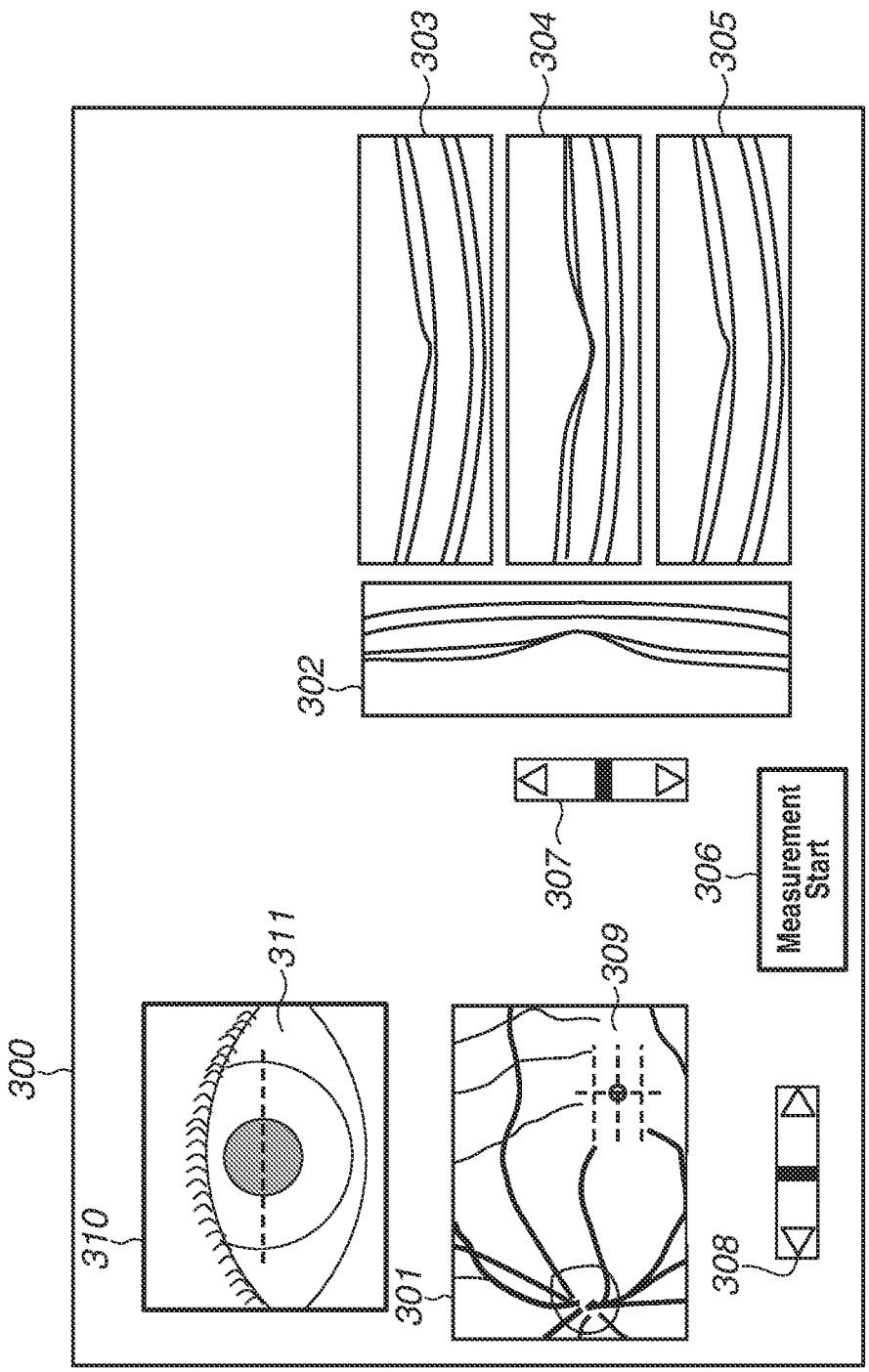

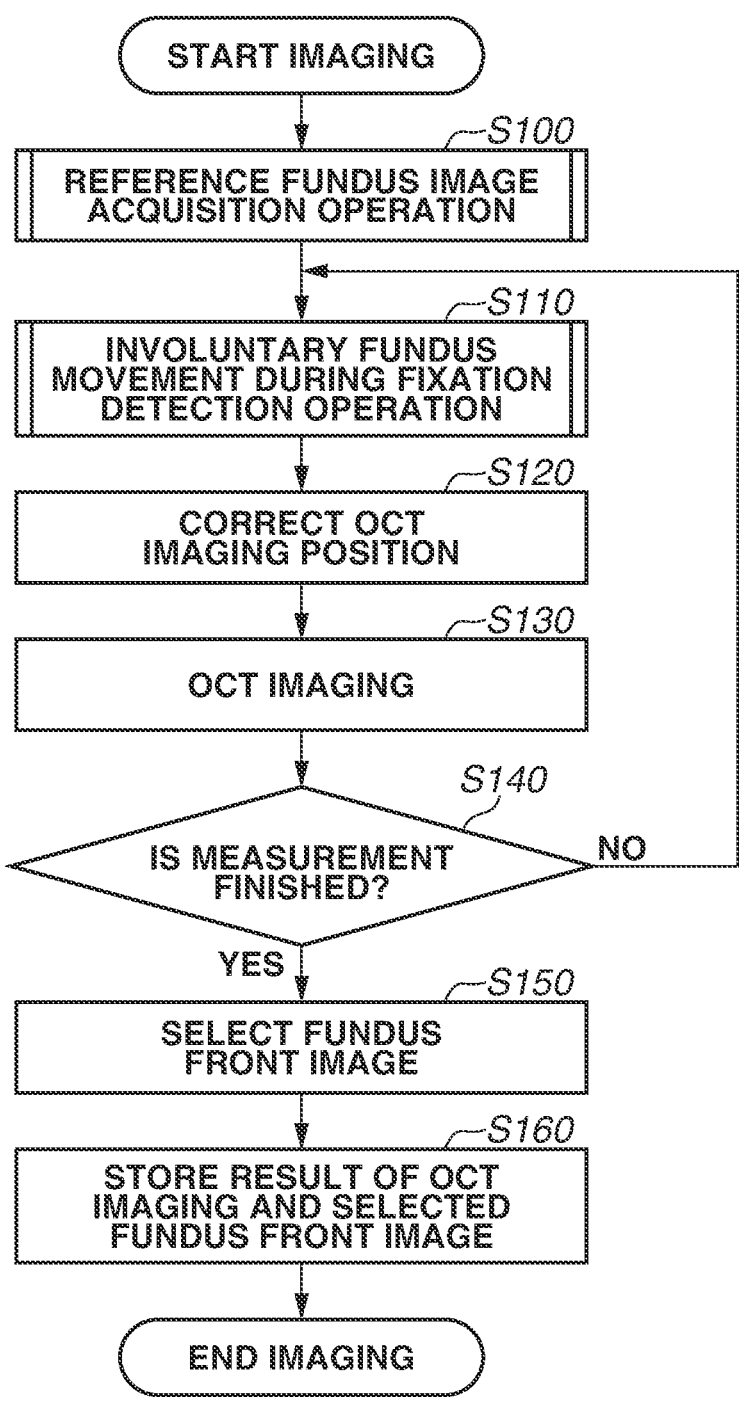

OPHTHALMIC APPARATUS

BACKGROUND OF THE INVENTION

Field of the Invention

The present invention relates to an ophthalmic apparatus and an ophthalmic method.

Description of the Related Art

Various ophthalmic instruments using optical devices are used today. For example, various devices are used as optical devices for observing an eye, including an anterior eye part imaging machine, a fundus camera, and a confocal scanning laser ophthalmoscope (SLO). Japanese Patent Application Laid-Open No. 7-178053 discusses a technique for increasing a frame rate to make flickering less noticeable using an interlace method in generating SLO images.

An optical coherence tomography (OCT) apparatus can capture a tomographic image of the retina on the fundus of an eye to be inspected at high resolution, so that OCT apparatuses are thus widely used for ophthalmological diagnosis of the retina. An apparatus configured by combining an OCT apparatus with an SLO is also known. The OCT apparatus presents the operator with a fundus front image for observation and a tomographic image for observation on an observation screen.

An image obtained by one OCT scan contains a lot of noise. The same location is therefore scanned a plurality of times, and the obtained images are arithmetically averaged for noise reduction. It takes time to perform multiple scans, and the eye to be inspected can move during imaging.

In view of this, it is important to correct the scanning position according to the movement of the eye to be inspected (fundus tracking) and maintain a constant positional relationship between the eye to be inspected and the apparatus main body. SLO images are often used for fundus tracking. In fundus tracking, the amount of change in position between SLO images over time is determined, and the imaging position of the OCT apparatus is corrected. The SLO images may simultaneously be stored as observation images during OCT inspection.

SUMMARY OF THE INVENTION

According to an aspect of the present invention, an ophthalmic apparatus includes a scanning unit configured to scan a fundus of a subject's eye with illumination light, a control unit configured to control the scanning unit to two-dimensionally scan a first field of the fundus with the illumination light and two-dimensionally scan a second field different from the first field with the illumination light so that scanning lines of the first field and scanning lines of the second field are alternately arranged in a direction crossing the scanning lines, a front image acquisition unit configured to obtain first front images of the fundus at different times using return light from the fundus in the first field, and obtain second front images of the fundus at different times using return light from the fundus in the second field, and a detection unit configured to, in a case where at least one of the first front images is selected as a reference image, detect movement of the subject's eye by using information indicating a position gap between the reference image and the first front images, and detect the movement of the subject's eye using information indicating a position gap between the reference image and the second front images and information indicating a difference in position between the first field and the second field.

Further features of the present invention will become apparent from the following description of exemplary embodiments with reference to the attached drawings.

BRIEF DESCRIPTION OF THE DRAWINGS

FIG. 3 is a diagram illustrating an observation screen according to an example of the present exemplary embodiment.

FIG. 4 is a flowchart for describing an imaging operation according to the first exemplary embodiment.

DESCRIPTION OF THE EMBODIMENTS

Figure 1A:
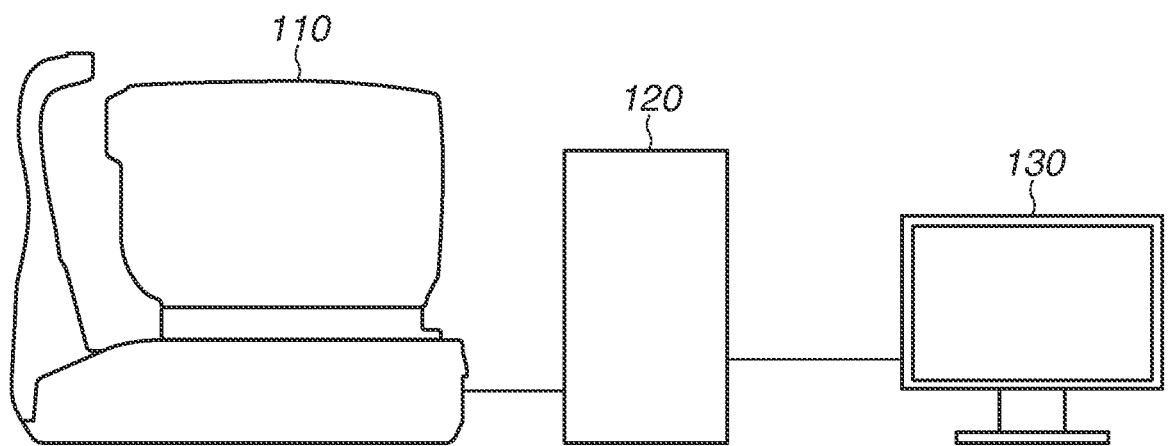
FIGS. 1A and 1B are block diagrams illustrating a functional configuration of an ophthalmic apparatus according to a first exemplary embodiment.

According to the interlace method, an image of an odd number field in which odd-numbered lines are obtained by odd-numbered scans and an image of an even number field in which even-numbered lines are obtained by even-numbered scans are alternately generated. In obtaining a position gap between front images of the fundus, such as scanning laser ophthalmoscope (SLO) images, according to the movement of the subject's eye, there occurs a deviation in position or a difference of one scanning line between the odd-numbered lines and the even-numbered lines.

According to an aspect of the present exemplary embodiment, a highly accurate determination of position gap between a plurality of front images of the fundus is obtained at different times using the interlace method.

In view of the foregoing, an ophthalmic apparatus according to the present exemplary embodiment includes a front image acquisition unit configured to obtain a plurality of first front images of the fundus at different times by using return light from the fundus in a first field, and obtain a plurality of second front images at different times by using the return light from the fundus in a second field. The ophthalmic apparatus according to the present exemplary embodiment also includes a detection unit configured to, if any one of the first front images is selected as a reference image, detect movement of the subject's eye by using information indicating a position gap between the reference image and the first front images, and detect the movement of the subject's eye by using information indicating a position gap between the reference image and the second front images and information indicating a difference in position between the first field and the second field.

According to the ophthalmic apparatus of the present exemplary embodiment, a position gap between a plurality of front images of the fundus, obtained at different times by the interlace method, can be obtained with high accuracy.

The present exemplary embodiment will be described in detail below with reference to the drawings.

When the ophthalmic apparatus according to the present exemplary embodiment obtains a plurality of front images of the fundus at different times, scanning lines of an odd number field in which odd-numbered lines are obtained by odd-numbered scans and scanning lines of an even number field in which even-numbered lines are obtained by even-numbered scans are alternately arranged in a direction crossing the scanning lines. The present invention is not limited to a case in which each individual scanning line is independently obtained. The first field of the fundus may be two-dimensionally scanned with the illumination light and the second field different from the first field may be two-dimensionally scanned with the illumination light so that the scanning lines of the first field and the scanning lines of the second field are alternately arranged in the direction crossing the scanning lines. For example, scans may be performed so that a forward scan of the first field and a backward scan of the second field cross each other, and a backward scan of the first field and a forward scan of the second field cross each other. For example, sine driving of a resonant scanner or zigzag driving of serrated shape may be employed.

In obtaining a position gap between the plurality of front images of the fundus, obtained at different times, a position gap in the vertical direction (sub scanning direction) which is the direction crossing the scanning lines can be obtained with high accuracy by taking a difference in position between the odd and even number fields into consideration. If at least one of the first front images corresponding to the first field is selected as the reference image, preferably, the first field is either one of the odd and even number fields, and the second field is the other.

FIG. 1A is a configuration diagram of an ophthalmic apparatus according to the present exemplary embodiment. The ophthalmic apparatus includes an imaging unit 110, an image processing unit 120, and a display unit 130. The imaging unit 110 captures image data by scanning and imaging a subject's eye with measurement light. The image processing unit 120 generates fundus images of the subject's eye from the image data obtained by the imaging unit 110. The display unit 130 displays the fundus images of the subject's eye, generated by the image processing unit 120. Here, the fundus images include a fundus front image and a tomographic image. A configuration of the imaging unit 110 will initially be described.

(Description of Imaging Unit 110)

Figure 2A:
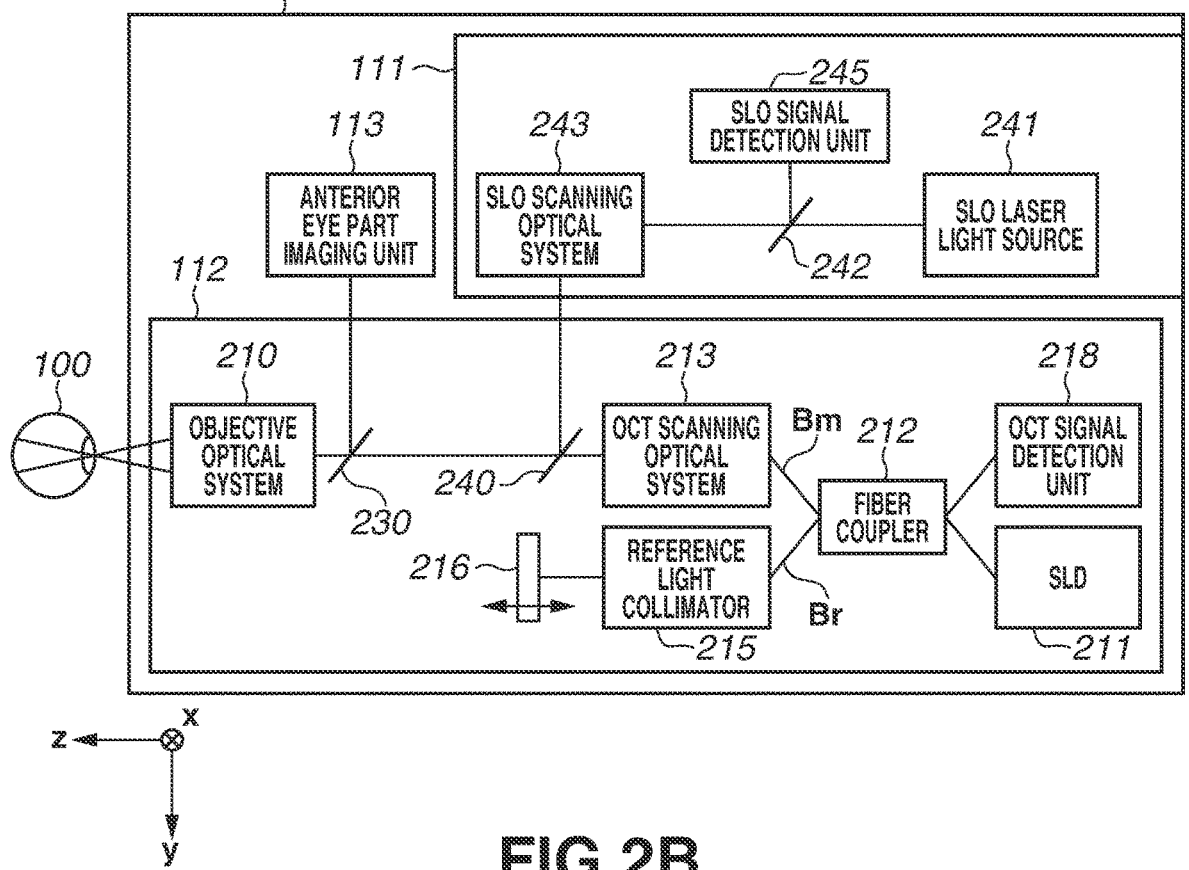
FIG. 2A is a block diagram illustrating a functional configuration of an imaging unit according to the first exemplary embodiment.

FIG. 2A illustrates the configuration of the imaging unit 110. The imaging unit 110 captures a two-dimensional image (fundus front image) of the fundus of a subject's eye 100, or captures a tomographic image of the fundus. In other words, the imaging unit 110 functions as an example of an imaging unit for capturing a fundus front image or a tomographic image of the subject's eye 100. FIG. 2A is a diagram illustrating an example of the configuration of the imaging unit 110. In the diagram, the imaging unit 110 includes a fundus front imaging unit 111 (an example of the front image acquisition unit), a tomographic image capturing unit 112 (an example of a tomographic image acquisition unit), and an anterior eye part imaging unit 113. The fundus front imaging unit 111 obtains a fundus front image of the subject's eye 100. The tomographic image capturing unit 112 scans a retina part with the measurement light to obtain a tomographic image. An objective optical system 210 is installed to be opposed to the subject's eye 100. A light splitting member 230 and a light splitting member 240 are arranged on the optical axis of the objective optical system 210. The light splitting members 230 and 240 branch an optical path of the tomographic image capturing unit 112, an optical path of the fundus front imaging unit 111, and an optical path of the anterior eye part imaging unit 113 by respective wavelength bands.

In the present exemplary embodiment, the fundus front imaging unit 111 is an interlaced SLO. The tomographic image capturing unit 112 is a spectral domain tomographic image capturing unit in which a signal detected by diffracting interference light is Fourier transformed to obtain a tomographic image. In the following description, a direction perpendicular to the plane of FIG. 2A will be referred to as an X-axis direction. A measurement light scan in the X-axis direction will be referred to as a horizontal scan, and a scan in a Y-axis direction will be referred to as a vertical scan.

In FIG. 2A, light emitted from a superluminescent diode (SLD) 211, which is a low coherence light source, is incident on a fiber coupler 212. The fiber coupler 212 splits the incident light into measurement light Bm and reference light Br corresponding to the measurement light Bm. The measurement light Bm is output to an OCT scanning optical system 213 through an optical fiber. The reference light Br is output to a reference light collimator 215. The OCT scanning optical system 213 is an example of another scanning unit different from one for obtaining a front image such as an SLO image. The OCT scanning optical system 213 condenses the input measurement light Bm on a not-illustrated galvano mirror to perform scanning of OCT measurement light. The galvano mirror here includes a scanner that performs a horizontal scan and a scanner that performs a vertical scan. The scanned measurement light Bm passes through the light splitting members 230 and 240 and reaches the retina of the subject's eye 100, which is a measurement target, via the objective optical system 210. The measurement light Bm is reflected here, passes through the objective optical system 210, the light splitting members 230 and 240, and the OCT scanning optical system 213 again, and reaches the fiber coupler 212.

Meanwhile, the reference light Br output from the fiber coupler 212 is reflected by a reference mirror 216 via an optical fiber and the reference collimator 215, and reaches the fiber coupler 212 again. Here, the reference light Br interferes with (is combined with) the measurement light Bm to generate interference light, which is input to an OCT signal detection unit 218. A position of the reference mirror 216 is changed to change an optical path length of the reference light Bm. The OCT signal detection unit 218 detects the interference light and outputs an electrical interference signal.

The fundus front imaging unit 111 and the light splitting member 240 capture an fundus front image. A light beam (illumination light) from an SLO laser light source 241 passes through a light splitting member 242 and is input to an SLO scanning optical system 243. The SLO scanning optical system 243 condenses the input SLO laser light (illumination light) on a not-illustrated scanner, which is an example of a scanning unit, and performs scanning of SLO measurement light. Here, the scanner includes a polygonal mirror which performs a horizontal scan (scan in a main scanning direction), and a galvano mirror which performs a vertical scan (scan in the sub scanning direction). Aside from the polygonal mirror, a resonant scanner may be used as a main scanning unit that performs a scan in the main scanning direction. That is, the SLO scanning optical system 243 may include a main scanning unit that scans the fundus with the illumination light in the main scanning direction in a reciprocating manner, and a sub scanning unit that scans the fundus with the illumination light at substantially constant speed. The main scanning unit may be a galvano mirror. The scanned SLO laser light (illumination light) passes through the light splitting members 230 and 240 and reaches the retina of the subject's eye 100, which is the measurement target, via the objective optical system 210. The SLO laser light is reflected here, passes the objective optical system 210, the light splitting members 230 and 240, the SLO scanning optical system 243, and the light splitting member 242 again, and reaches an SLO signal detection unit 245. The SLO signal detection 245 detects the light and outputs an electrical SLO signal.

The anterior eye part imaging unit 113 includes a not-illustrated infrared light-emitting diode (LED) which illuminates the anterior eye part, and a not-illustrated charge-coupled device (CCD) camera. The infrared LED irradiates the anterior eye part of the subject with generated infrared light via the light splitting member 230 and the objective optical system 210. Reflected infrared light passes the objective optical system 210 and the light splitting member 230, and the CCD camera obtains an anterior eye part image.

The SLO laser light source 241 has a wavelength of 750 nm. The SLD 211 has a wavelength of 850 nm. The infrared light for illuminating the anterior eye part has a wavelength of 970 mm. However, the present invention is not limited to such wavelengths. For example, other wavelengths may be used for the OTC, SLO, and anterior eye part illumination.

The light splitting members 230 and 240 are dichroic mirrors. The light splitting member 242 is a perforated mirror. Such mirrors are merely an example. Members that can split a light beam into two, like a half mirror, may be used.

Figure 2B:
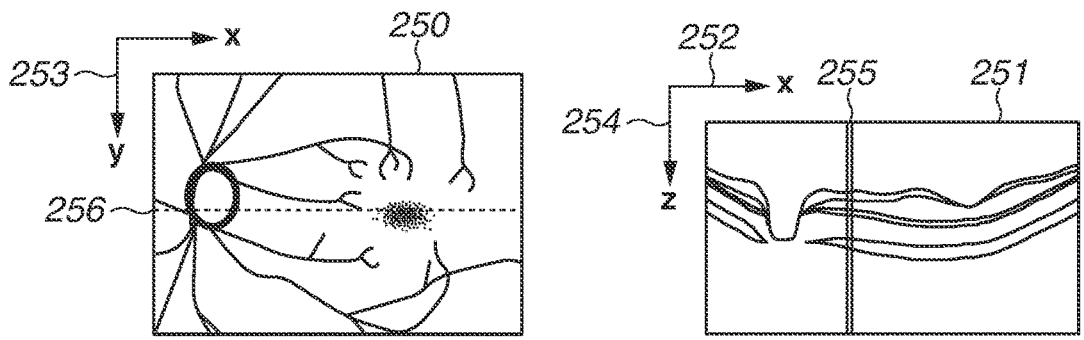
FIG. 2B illustrates a tomographic image a fundus front image according to the first exemplary embodiment and, respectively.

FIG. 2B is a diagram for describing a tomographic image reconstructed by the imaging unit 110 and a fundus front image. FIG. 2B illustrates an example of a fundus front image 250 of the subject's eye 100, obtained by the imaging unit 110, and an example of a tomographic image 251 of the retina, obtained by the imaging unit 110. An arrow 252 indicates a horizontal scanning direction. An arrow 253 indicates a vertical scanning direction. An arrow 254 indicates a depth direction of an A-scan 255. A dotted line 256 on the fundus front image 250 indicates the position in which the tomographic image 251 is captured.

In the present exemplary embodiment, a Michelson interferometer is used as the interferometer. However, a Mach-Zehnder interferometer may be used. According to a difference in light quantity between the measurement light Bm and the reference light Br, the Mach-Zehnder interferometer is desirably used if the difference in light quantity is large. The Michelson interferometer is desirably used if the difference in light quantity is relatively small. The present invention is also applicable to optical arrangements and apparatus configurations other than those discussed above of the present exemplary embodiment. For example, the present exemplary embodiment uses a spectral domain (SD) OCT apparatus among Fourier domain (FD) OCT apparatuses. However, the present exemplary embodiment may be applied to OCT apparatuses of other methods. In particular, the present exemplary embodiment may be applied to a swept source (SS) OCT apparatus using a wavelength-swept light source.

(Description of Image Processing Unit)

Figure 1B:
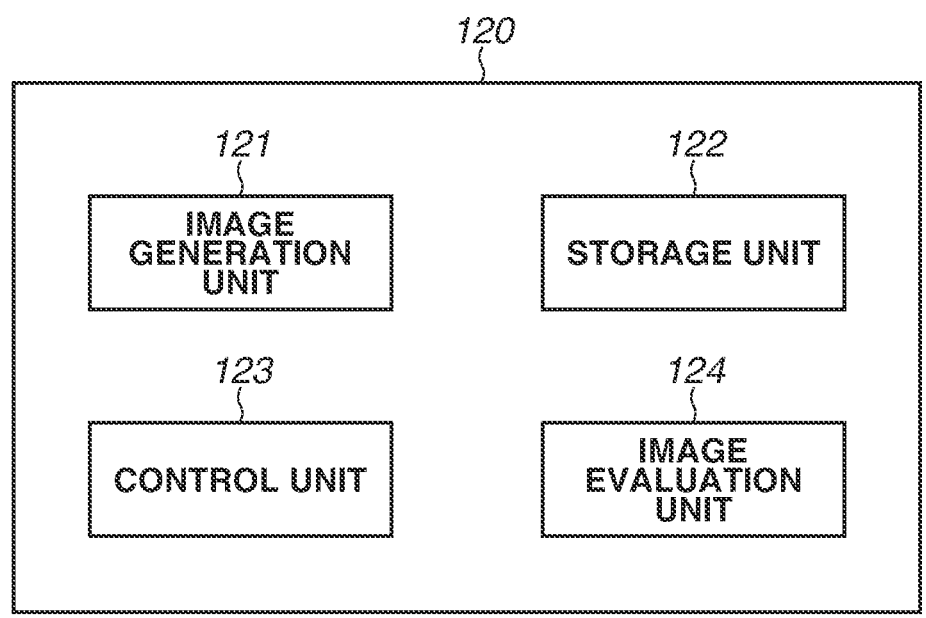

Next, the image processing unit 120 will be described. FIG. 1B illustrates a configuration of the image processing unit 120. The image processing unit 120 includes an image generation unit 121, a storage unit 122, a control unit 123, and an image evaluation unit 124. The control unit 123 controls the imaging unit 110 to capture an image of the subject's eye 100. The control unit 123 transmits a scan control signal to the OCT scanning optical system 213 so that the subject's eye 100 is scanned in X and Y directions. The control unit 123 further performs position control on a not-illustrated focus lens and the reference mirror 216. The image generation unit 121 is connected to the OCT signal detection unit 218, the SLO signal detection unit 245, and the storage unit 122 in the image processing unit 120. The control unit 123 performs two-dimensional correlation calculation on a plurality of SLO images. The control unit 123 can use a result of the two-dimensional correlation calculation to determine an amount of displacement between the SLO images. The control unit 123 performs a fundus tracking operation by correcting an OCT imaging position as much as the determined amount of displacement. The image generation unit 121 performs Fourier transform on data obtained from the OCT signal detection unit 218, and converts the Fourier-transformed data into luminance or density information, and an image of the subject's eye 100 in a depth direction (Z direction) is obtained. Such a scan method will be referred to as an A-scan. The obtained tomographic image will be referred to as an A-scan image. The OCT scanning optical system 213 scans the subject's eye 100 with such an A-scan in a predetermined transverse direction, and a plurality of A-scan images are obtained. For example, if the OCT scanning optical system 213 scans the subject's eye 100 in the X direction, a tomographic image on an XZ plane is obtained. Scanning in the Y direction obtains a tomographic image on a YZ plane. Such a method for scanning the subject's eye 100 in a predetermined transverse direction will be referred to as a B-scan. The obtained tomographic image will be referred to as a B-scan image. If the OCT scanning optical system 213 repeats the B-scan in a predetermined direction of the subject's eye 100, a plurality of B-scan images can be obtained. For example, if the OCT scanning optical system 213 repeats the B-scan on the XZ plane in the Y direction, three-dimensional information about the XYZ space can be obtained. Such a scan will be referred to as a C-scan. Data including the obtained plurality of B-scan images will be referred to as three-dimensional data. The storage unit 122 stores the images generated by the image generation unit 121. Alternatively, the storage unit 122 stores imaging parameters used in capturing the images of the subject's eye 100. The image evaluation unit 124 evaluates the images generated by the image generation unit 121 or the images stored in the storage unit 122. Evaluation is made based on parameters such as sharpness and an average luminance value of the entire images. The higher the sharpness, the higher the evaluation. Other evaluation criteria include that the average luminance value is greater than or equal to a predetermined value so that the average luminance value will not be too low. The image evaluation unit 124 further determines image defects. Examples of the image defects to be determined include "blinking traces" which remain in an image due to blinking of the subject's eye 100 during imaging, "interlace stripes" due to involuntary eye movement during fixation, and insufficient contrast.

(Method for Generating Fundus Front Image by Interlace Method)

Next, a method for generating a fundus front image will be described. The control unit 123 transmits a scan control signal to the SLO scanning optical system 243 so that the subject's eye 100 is scanned in the X and Y directions. The control unit 123 further performs position control on the not-illustrated focus lens. The image generation unit 121 generates a fundus front image in the X and Y directions by arranging luminance values obtained from signal information obtained from the SLO signal detection unit 245 based on a scanning signal. Here, the image generation unit 121 generates an interlaced fundus front image while controlling the SLO scanning optical system 243 which scans the fundus. The image evaluation unit 124 analyzes and evaluates the fundus front image. The storage unit 122 is connected with the image generation unit 121 and the display unit 130. The image generation unit 121 generates and stores B-scan images, three-dimensional data, the fundus front image, and an anterior eye part image into the storage unit 122. The display unit 130 displays the B-scan images, the fundus front image, and the anterior eye part image stored in the storage unit 122 as an observation screen. A procedure from observation to imaging by the ophthalmic apparatus including the imaging unit 110, the image processing unit 120, and the display unit 130 described above will be described.

The observation screen will be described with reference to FIG. 3. FIG. 3 illustrates an observation screen 300 displayed on the display unit 130 during observation. The observation screen 300 includes an anterior eye part image 310, a fundus front image 301, tomographic images 302, 303, 304, and 305, a focus adjustment slider 308, a reference mirror position adjustment slider 307, and a measurement start button 306. Dotted lines (scan lines) 309 indicate the scan positions of the tomographic images 302, 303, 304, and 305 on the fundus front image 301. A not-illustrated operator positions the subject's eye 100 in front of the objective optical system 210 while observing the anterior eye part image 310. The SLO scanning optical system 243 then performs scans in the X and Y directions to generate the fundus front image 301, and the OCT scanning optical system 213 performs scan in the X and Y directions to generate the tomographic images 302, 303, 304, and 305. The operator operates the focus adjustment slider 308 and the reference mirror position adjustment slider 307 by using a not-illustrated mouse and mouse cursor while observing the fundus front image 301 and the tomographic images 302, 303, 304, and 305. The operator therewith adjusts the focus of the tomographic images 302, 303, 304, and 305, and the position of the reference mirror 216. The tomographic images 302, 303, 304, and 305, and the fundus front image 301 are updated as appropriate. The scan lines 309 in the fundus front image 301 indicate the scan positions at which the subject's eye 100 is scanned when the tomographic images 302, 303, 304, and 305 are obtained. The scan lines 309 are superimposed on the fundus front image 301. The operator operates the scan lines 309 by using a not-illustrated scan position change unit such as a mouse and a touch panel, and therewith sets desired scan positions.

(Flowchart of Fundus Front Image Generation Operation)

Next, detailed processing for generating a fundus front image by the ophthalmic apparatus according to the present exemplary embodiment will be described with reference to the flowchart illustrated in FIG. 4. In the present exemplary embodiment, to increase the frame rate, scans for capturing a fundus front image are performed by the interlace method.

Figure 2C:
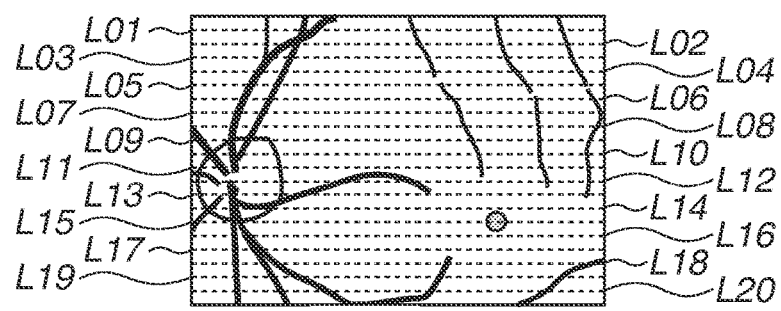
FIG. 2C illustrates a fundus front image divided by odd-numbered lines and even-numbered lines according to the first exemplary embodiment.

By the interlace method, an obtained image is divided by odd-numbered lines obtained by odd-numbered scans and even-numbered lines obtained by even-numbered scans. FIG. 2C illustrates an example thereof. As illustrated in FIG. 2C, an fundus front image of the odd-numbered lines is an example of a first front image, and includes lines L1, L3, . . . , L19. A fundus front image of the even-number lines is an example of a second front image, and includes lines L2, L4, . . . , L20. The fundus front image of the odd-numbered lines and the fundus front image of the even-numbered lines will be referred to an image of an odd number field in which the odd-numbered lines are obtained and an image of an even number field in which the even-numbered lines are obtained, respectively. FIG. 4 is a flowchart of an OCT imaging sequence which is started by pressing the measurement start button 306.

<Step S100>

In step S100, the control unit 123 controls the fundus front imaging unit 111, and the image generation unit 121 obtains a reference fundus image for performing fundus tracking. Details of the operation for obtaining the reference fundus image (reference fundus image acquisition operation) will be described below.

<Step S110>

In step S110, the control unit 123 detects an amount of involuntary movement of the subject's eye 100 during fixation by detecting a change in position of a fundus front image over time. Details of such a detection operation of involuntary eye movement during fixation will be described below. In step S110, the fundus front image used in detecting the amount of involuntary eye movement during fixation is also stored in the storage unit 122.

<Step S120>

In step S120, the control unit 123 corrects the OCT imaging position by changing the OCT imaging position as much as the amount of involuntary eye movement during fixation, detected in step S110. Specifically, the control unit 123 corrects the OCT imaging position by changing the scan control signal given to the OCT scanning optical system 213.

<Step S130>

In step S130, the control unit 123 controls the tomographic image capturing unit 112 to obtain a fundus tomographic image (B-scan image) of the subject's eye 100.

<Step S140>

In step S140, the control unit 123 determines whether the measurement is finished. Since an OCT image contains a lot of noise, measurement is performed a plurality of times, and the measurement results are added and averaged for noise reduction. A fundus three-dimensional image (C-scan image) can be obtained by obtaining B scan images a plurality of times while shifting positions as described above, and combining the obtained data. Whether the measurement is finished is determined depending on whether a predetermined number of B-scans have been finished, or whether a predetermined area has been scanned. If the measurement is finished (YES in step S140), the processing proceeds to step S150. If the measurement is not finished (NO in step S140), the processing proceeds to step S110. The foregoing operation is then repeated until the measurement is finished.

<Step S150>

In step S150, the control unit 123 selects an image evaluated the most highly among the series of SLO images stored in step S110 as a fundus front image during OCT imaging. The SLO images are evaluated by the image evaluation unit 124. The evaluation criteria include the intensity of the sharpness and that the average luminance value is greater than or equal to a predetermined value.

<Step S160>

In step S160, the control unit 123 stores the result of the OCT imaging and the fundus front image selected in step S150 into the storage unit 122. The fundus front image generation operation ends here.

(Flowchart of Reference Fundus Image Acquisition Operation)

Figure 5:
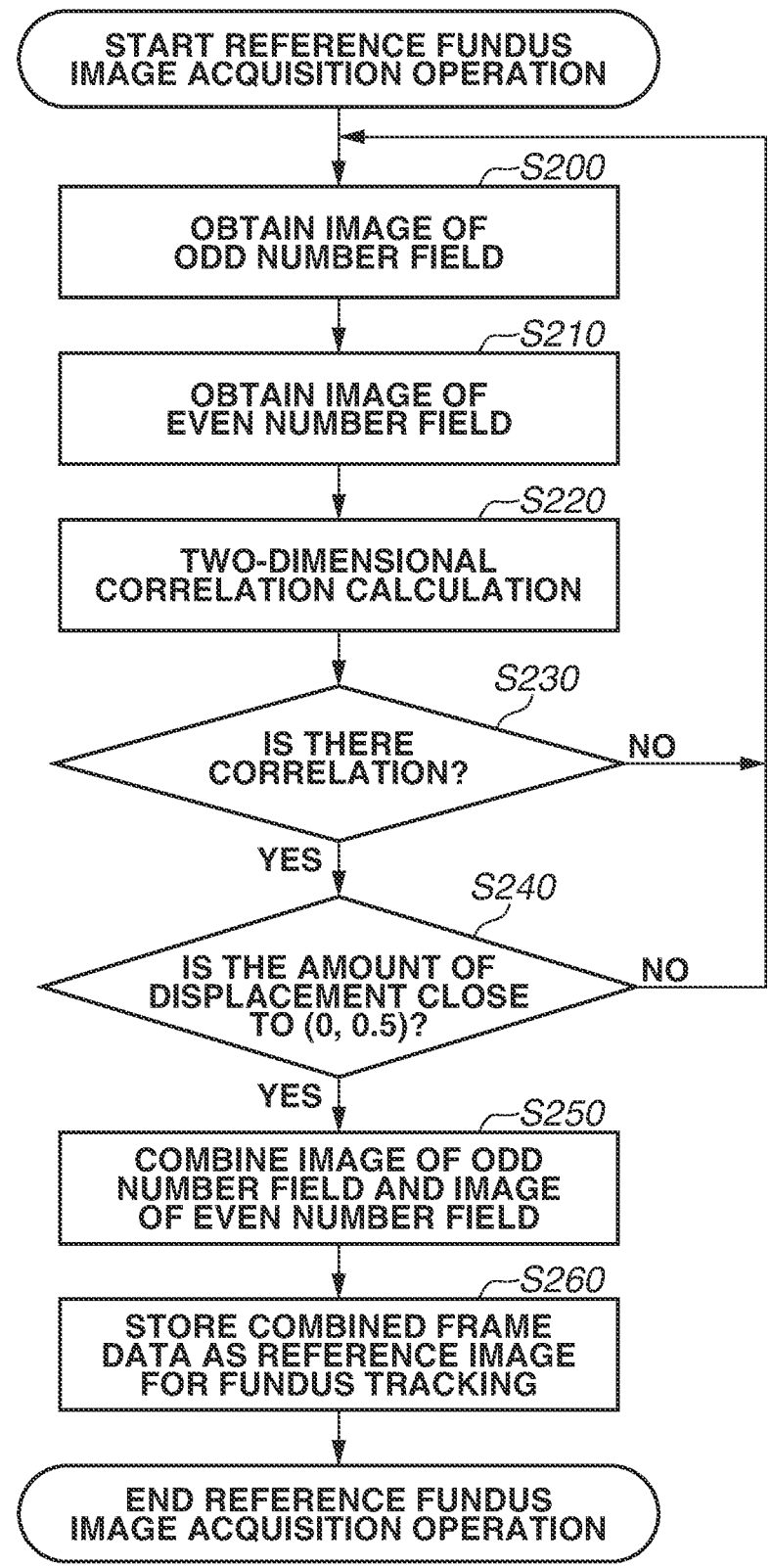
FIG. 5 is a flowchart for describing a reference fundus image acquisition operation according to the first exemplary embodiment.

Next, the reference fundus image acquisition operation of step S100 will be described with reference to the flowchart of FIG. 5.

<Step S200>

In step S200, the control unit 123 controls the fundus front imaging unit 111, and the image generation unit 121 obtains an image of the odd number field in which the odd-numbered lines are obtained.

<Step S210>

In step S210, the control unit 123 controls the fundus front imaging unit 111, and the image generation unit 121 obtains an image of the even number field in which the even-numbered lines are obtained.

<Step S220>

In step S220, the control unit 123 performs two-dimensional correlation calculation between the image of the odd number field and the image of the even number field. The two-dimensional correlation calculation is performed in the following manner. A cross-correlation coefficient between image 1 $I_1(X, Y)$ and image 2 $I_2(X, Y)$ is defined by the following Equation (1):

$$R_{12}(u, v) = \iint I_1(X, Y) I_2(X+u, Y+v) dX dY. \quad (1)$$

If the cross-correlation coefficient has a clear peak, the peak position $(u_0, v_0)$ indicates the amount of displacement between image 1 and image 2. The presence or absence of correlation can be determined by comparing $R_{12}(u, v)$ at the peak position of Equation (1) with a predetermined threshold. Aside from such a cross-correlation method, a highest degree of matching can be determined by other known methods. Examples include a minimax approximation algorithm. Such other methods may be used in the present exemplary embodiment. While the correlation calculation itself is performed in units of pixels, the amount of displacement can be determined in units of subpixels by performing an interpolation calculation based on several points near the peak of the correlation coefficient.

Figure 6A:
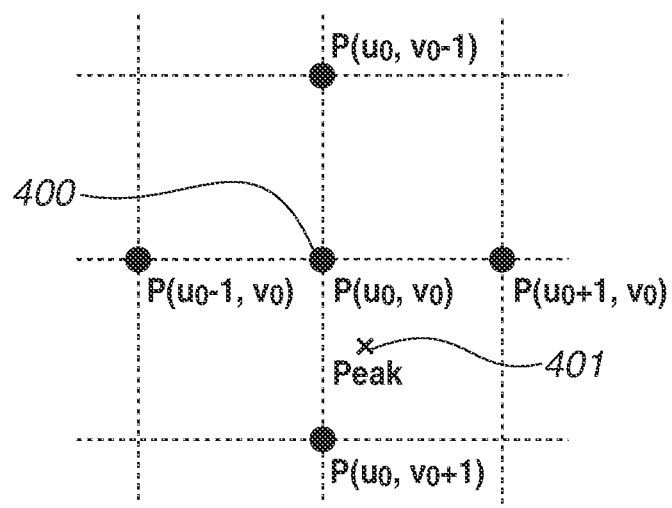
FIGS. 6A and 6B are diagrams for describing a subpixel interpolation operation according to the first exemplary embodiment.
Figure 6B:
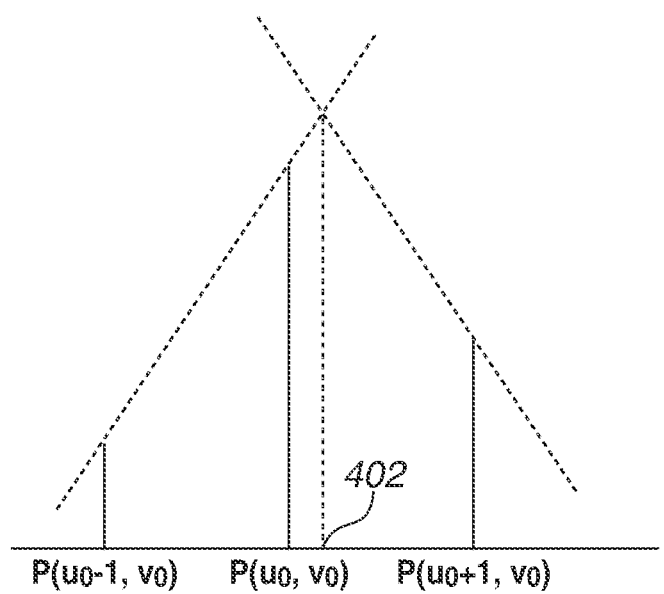

FIGS. 6A and 6B are diagrams for describing subpixel interpolation. FIG. 6A is a diagram illustrating the vicinity of an original peak 401 of the correlation coefficient. FIG. 6A illustrates a pixel $P(u_0, v_0)$ (400) representing a peak of the correlation calculation, and adjoining pixels. To determine the position of the peak 401, a linear interpolation illustrated in FIG. 6B is performed in both the X- and Y-axis directions. FIG. 6B is a diagram in which the pixel $P(u_0, v_0)$ and adjoining pixels $P(u_0-1, v_0)$ and $P(u_0+1, v_0)$ in the X-axis direction are plotted on the horizontal axis, and the correlation coefficient thereof on the vertical axis. Draw lines between the pixel $P(u_0, v_0)$ representing the peak of the correlation calculation and the respective adjoining pixels $P(u_0-1, v_0)$ and $P(u_0+1, v_0)$. Adopt one having the higher gradient. In FIG. 6B, the line connecting the pixels $P(u_0-1, v_0)$ and $P(u_0, v_0)$ is adopted. Then, draw a line from the remaining point, with a gradient having the same absolute value as and reverse polarity to those of the adopted line. The coordinate of the intersection of the two lines (in FIG. 6B, intersection 402) is assumed as the X coordinate of the original peak 401. Perform a similar interpolation calculation on the Y-axis. In such a manner, the X and Y coordinates of the peak 401 can be determined in units of subpixels. While linear interpolations are described to be performed here, a quadratic function passing through the three points may be generated, and an extreme value thereof may be determined. Other interpolation methods may be used. Examples include interpolating a greater number of points around the peak with a three-dimensional curved surface and determining the peak thereof.

<Step S230>

In step S230, the control unit 123 determines the presence or absence of correlation by comparing the correlation coefficient obtained from the result of the correlation calculation in step S220 with a predetermined threshold. The value of the correlation coefficient becomes small if the image acquisition of at least either one of the fields is affected by blinking or eye movement due to involuntary eye movement during fixation. If there is no correlation (NO in step S230), the processing returns to step S200. The image generation unit 121 then obtains the field images again. If there is a correlation (YES in step S230), the processing proceeds to step S240.

<Step S240>

In step S240, the control unit 123 determines whether the amount of displacement obtained from the result of the correlation calculation in step S220 is close to (0, 0.5). The amount of displacement in the X direction is in units of pixels. The amount of displacement in the Y direction is in units of scanning lines of the interlaced fields. That is, 1 in the Y direction is equivalent to two scanning lines of the frame image. In other words, 0.5 in the Y direction corresponds to the amount of displacement between the odd number field and the even number field. If the amount of displacement is close to (0, 0.5) (YES in step S240), the processing proceeds to step S250. If the amount of displacement is large (NO in step S240), the processing returns to step S200. The image generation unit 121 then obtains the images of the fields again.

<Step S250>

In step S250, the image generation unit 121 combines the image of the odd number field obtained in step S200 and the image of the even number field obtained in step S210 to generate frame data of an fundus front image (new front image). The image data on the odd number field is combined to be the odd-numbered lines of the combined frame data. The image data on the even number field is combined to be the even-numbered lines of the combined frame data. In other words, the odd-numbered lines are areas corresponding to the image data on the odd number field of the new front image. The even-numbered lines are areas corresponding to the image data on the even number field of the new front image.

<Step S260>

In step S260, the control unit 123 stores the frame data combined in step S250 into the storage unit 122 as a reference image for fundus tracking.

In such a manner, a frame image obtained by combining the image of the odd number field and the image of the even number field and having a small amount of displacement therebetween can be used as the reference image for fundus tracking. This can increase the resolution in the vertical direction, compared to when a field image is used as the reference image in detecting the amount of involuntary eye movement during fixation as will be described below. By taking the image quality of the reference image into consideration, an image with less distortion due to the movement of the subject's eye 100 can be selected as the reference image. A position gap, namely a positional shift or displacement between two images, can thus be obtained with higher accuracy.

In the description of the present exemplary embodiment, the images of the odd and even number fields are described to be obtained as a set. However, the correlation may be sequentially determined field by field. If, in step S240, correlation is determined of an image of the odd number field to an image of the even number field, the result of the correlation calculation may be compared with the amount of displacement (0, 0.5). If the correlation is determined of an image of the even number field to an image of the odd number field, the result of the correlation calculation may be compared with an amount of displacement (0, −0.5).

(Flowchart of Detection Operation of Involuntary Eye Movement during Fixation)

Next, the detection operation of involuntary eye movement during fixation in step S110 will be described with reference to the flowchart of FIG. 7. The following description deals with an example in which an SLO image starts to be scanned at the line LO1 as illustrated in FIG. 2C. With the odd number field as a reference, no offset is thus added in determining correlation between the reference image and the odd number field. An offset is added in determining correlation between the reference image and the even number field.

<Step S300>

Figure 7:
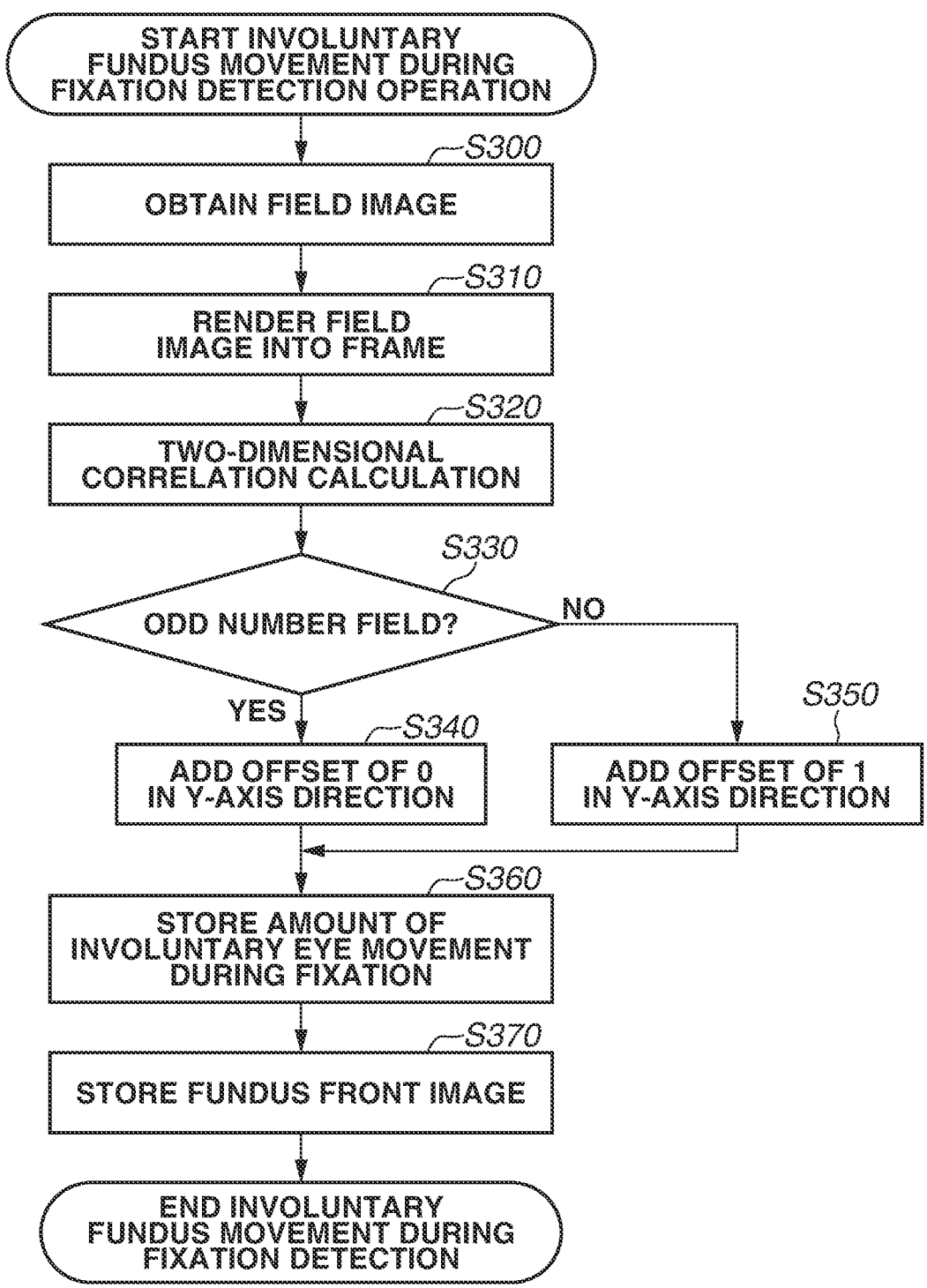
FIG. 7 is a flowchart for describing a detection operation of involuntary eye movement during fixation according to the first exemplary embodiment.

If the detection operation of involuntary eye movement during fixation in step S110 is started, the operation according to the flowchart of FIG. 7 is started. In step S300, the control unit 123 initially controls the fundus front imaging unit 111, and the image generation unit 121 obtains a field image.

<Step S310>

In step S310, the control unit 123 renders the field image (field data) obtained in step S300 into a frame. Such framing is performed in the following manner. Initially, prepare a data area having lines twice as many as the number of lines of the field data. Next, copy data on nth lines of the field data to (2n−1)th lines of the data area. Copy the data on the (2n−1)th lines of the data area to (2n)th lines. Accordingly, scanning line data of the field data is doubled. The term "copy" is used since the scanning line data of the field data is written to the scanning lines of the frame data twice. In such a manner, image data having the number of lines twice that of the field data (equivalent to that of frame data) and of which the odd-numbered lines and the subsequent even-numbered lines have the same data can be prepared.

<Step S320>

In step S320, the control unit 123 performs two-dimensional correlation calculation between the reference fundus image obtained in step S100 and the fundus front image rendered into a frame in step S310. Since the correlation calculation here is correlation calculation on frame data, the amount of displacement in the X direction is unchanged, i.e., in units of pixels. The amount of displacement in the Y direction is in units of one scanning line. The two-dimensional correlation calculation determines an amount of displacement in units of subpixels according to the method described in step S220.

<Step S330>

In step S330, the control unit 123 determines whether the field image obtained in step S300 is an image of the odd number field. If the field image is an image of the odd number field (YES in step S330), the processing proceeds to step S340. If not, i.e., the field image is an image of the even number field (NO in step S330), the processing proceeds to step S350.

<Step S340>

If the field image is an image of the odd number field, then in step S340, the control unit 123 adds no offset in the Y-axis direction (i.e., an offset of 0). The processing proceeds to step S360.

<Step S350>

If the field image is an image of the even number field, then in step S350, the control unit 123 adds an offset of 1 in the Y-axis direction. The processing proceeds to step S360. The offset of 1 is intended to take a difference in position between the odd and even number fields into consideration.

<Step S360>

By the foregoing operation, the amount of displacement between the reference image and the fundus front image (field image) obtained in step S300, i.e., the amount of involuntary movement of the subject's eye 100 during fixation is determined. In step S360, the control unit 123 stores the determined amount of involuntary eye movement during fixation into the storage unit 122.

<Step S370>

In step S370, the control unit 123 sequentially stores the fundus front image obtained in step S300 into the storage unit 122. As described in step S150, the fundus front image in storing the result of the OCT imaging is selected from a series of fundus front images stored here. The detection operation of involuntary eye movement during fixation ends.

By such a configuration, the accuracy of the fundus tracking in the vertical direction can be improved. The fundus front image to be stored in recording the result of the OCT imaging is selected from the fundus front images stored during the OCT imaging. This provides the effect that the measurement time can be reduced, compared to when a fundus front image to be stored is obtained in recording the result of the OCT imaging.

In the foregoing description, the odd number field is described to be used as a reference. However, the even number field may be used as a reference. In such a case, no offset is added if correlation is determined between the reference image and the even number field. An offset (for example, an offset of −1 in the Y-axis direction) is added if correlation is determined between the reference image and the odd number field.

In the present exemplary embodiment, the odd number field and the even number field are described to be combined into a reference frame image serving as the reference fundus image. However, an uncombined field image may be used as the reference image. In such a case, the image evaluation unit 124 evaluates the sharpness and the average luminance values of the odd and even number fields, and selects the more highly evaluated field as the reference image. If the odd number field is selected as the reference image, an offset of 0 is added in determining correlation with the odd number field. An offset of 0.5 is added in the Y direction in determining correlation with the even number field. If the even number field is selected as the reference image, an offset of −0.5 is added in the Y direction in determining correlation with the odd number field. An offset of 0 is added in determining correlation with the even number field. The offsets are in units of scanning lines of the fields of interlacing. The correlation is determined in units of subpixels. In such a manner, the tracking accuracy in the vertical direction can be easily increased in consideration of a difference in position between the odd and even number fields. If the odd number field is selected as the reference image, correlation may be determined with only the odd number fields of the SLO images. If the even number field is selected as the reference image, correlation may be determined with only the even number fields of the SLO images. With such a configuration, the offset processing can be simplified.

Figure 8:
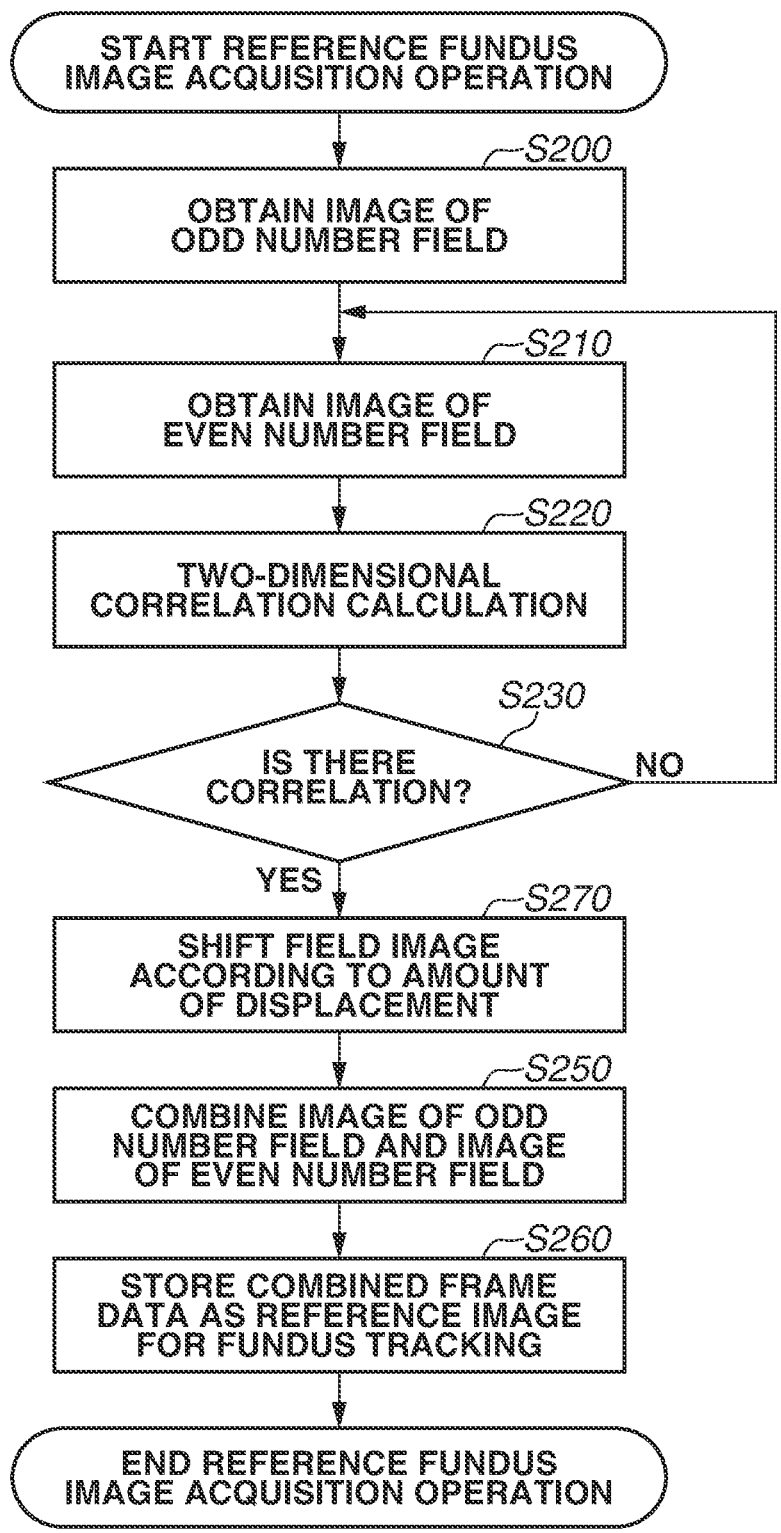
FIG. 8 is a flowchart for describing a reference fundus image acquisition operation according to another exemplary embodiment.

In the operation for obtaining the reference fundus image according to the foregoing exemplary embodiment, field images having a small amount of displacement are combined to obtain the reference fundus image. Instead, field images may be shifted according to the amount of displacement determined by correlation calculation, and combined into a reference image. FIG. 8 is a flowchart for describing another operation for obtaining the reference fundus image. Blocks for performing operations similar to those of FIG. 5 are designated by the same reference numerals. A description thereof will be omitted. In step S230, if there is a correlation (YES in step S230), the processing proceeds to step S270. In step S270, the control unit 123 shifts either one of the field images according to the amount of displacement determined in step S220. The processing proceeds to step S250. In step S250, the control unit 123 combines the shifted field image and the other field image to obtain a reference image. The reference image can be obtained even if the displacement is large. This provides the effect of reducing the measurement time.

The present invention is not limited to the description of the foregoing exemplary embedment, and various modifications may be made within the scope of the claims. While an OCT is used for the ophthalmic apparatus, the present invention is not limited thereto. A noncontact tonometer, an eye refractive power measurement device, and a fundus camera may be used. Exemplary embodiments of the present invention are applicable to ophthalmic apparatuses in general, including an SLO, an OCT, and a fundus camera using an adaptive optics system.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-237684, filed Dec. 7, 2016, which is hereby incorporated by reference herein in its entirety.

What is claimed is:

1. An ophthalmic apparatus comprising:
   a scanning unit configured to scan a fundus of a subject's eye with illumination light;
   a control unit configured to control the scanning unit to two-dimensionally scan a first field of the fundus with the illumination light and two-dimensionally scan a second field different from the first field with the illumination light so that scanning lines of the first field and scanning lines of the second field are alternately arranged in a direction crossing the scanning lines;
   a front image acquisition unit configured to obtain first front images of the fundus at different times using return light from the fundus in the first field, and obtain second front images of the fundus at different times using return light from the fundus in the second field; and
   a detection unit configured to, in a case where at least one of the first front images is selected as a reference image, detect movement of the subject's eye using information indicating a position gap between the reference image and the first front images, and detect the movement of the subject's eye using information indicating a position gap between the reference image and the second front images and information indicating a difference in position between the first field and the second field.

2. The ophthalmic apparatus according to claim 1, wherein the first field is either one of an odd number field in which odd-numbered lines scanned in odd-numbered turns are obtained and an even number field in which even-numbered lines scanned in even-numbered turns are obtained, and
   wherein the second field is the other field of said either one.

3. The ophthalmic apparatus according to claim 1, wherein the control unit is configured to control the scanning unit so that a forward scan of the first field and a backward scan of the second field cross each other, and a backward scan of the first field and a forward scan of the second field cross each other.

4. The ophthalmic apparatus according to claim 3, wherein the scanning unit includes a main scanning unit configured to scan the fundus with the illumination light by forward and backward scans in a main scanning direction, and a sub scanning unit configured to scan the fundus with the illumination light at substantially constant speed.

5. The ophthalmic apparatus according to claim 1, further comprising:
   an OCT scanning unit configured to scan the fundus with measurement light; and
   a tomographic image acquisition unit configured to obtain a tomographic image of the fundus by using light obtained by combining return light from the fundus irradiated with the measurement light and reference light corresponding to the measurement light,
   wherein the control unit is configured to control the OCT scanning unit using information indicating the detected movement.

6. The ophthalmic apparatus according to claim 1, further comprising a selection unit configured to select one of the first front images and the second front images as the reference image.

7. The ophthalmic apparatus according to claim 1, further comprising:
a generation unit configured to generate a new front image using the first front images and the second front images; and
a selection unit configured to select an area corresponding to the first front images in the new front image as the reference image.

8. The ophthalmic apparatus according to claim 1, wherein the detection unit is configured to obtain information indicating the position gap between the reference image and the first front images by performing two-dimensional correlation calculation between the reference image and the first front images, and obtain information indicating the position gap between the reference image and the second front images by performing two-dimensional correlation calculation between the reference image and the second front images.

9. The ophthalmic apparatus according to claim 8, wherein the detection unit is configured to perform the two-dimensional correlation calculation in units of subpixels.

10. An ophthalmic apparatus comprising:
a scanning unit configured to scan a fundus of a subject's eye with illumination light;
a control unit configured to control the scanning unit to two-dimensionally scan a first field of the fundus with the illumination light and two-dimensionally scan a second field different from the first field with the illumination light so that scanning lines of the first field and scanning lines of the second field are alternately arranged in a direction crossing the scanning lines;
a front image acquisition unit configured to obtain first front images of the fundus at different times using return light from the fundus in the first field, and obtain second front images of the fundus at different times using return light from the fundus in the second field; and
a detection unit configured to, in a case where at least one of the first front images is selected as a reference image, detect movement of the subject's eye using information indicating a position gap between the reference image and the first front images, and in a case where at least one of the second front images is selected as the reference image, detect the movement of the subject's eye using information indicating a position gap between the reference image and the second front images.

11. A method for controlling an ophthalmic apparatus including a scanning unit configured to scan a fundus of a subject's eye with illumination light, the method comprising:
controlling the scanning unit to two-dimensionally scan a first field of the fundus with the illumination light and two-dimensionally scan a second field different from the first field with the illumination light so that scanning lines of the first field and scanning lines of the second field are alternately arranged in a direction crossing the scanning lines;
obtaining first front images of the fundus at different times using return light from the fundus in the first field, and obtaining second front images of the fundus at different times using return light from the fundus in the second field; and
in a case where at least one of the first front images is selected as a reference image, detecting movement of the subject's eye using information indicating a position gap between the reference image and the first front images, and detecting the movement of the subject's eye using information indicating a position gap between the reference image and the second front images and information indicating a difference in position between the first field and the second field.

12. A method for controlling an ophthalmic apparatus including a scanning unit configured to scan a fundus of a subject's eye with illumination light, the method comprising:
controlling the scanning unit to two-dimensionally scan a first field of the fundus with the illumination light and two-dimensionally scan a second field different from the first field with the illumination light so that scanning lines of the first field and scanning lines of the second field are alternately arranged in a direction crossing the scanning lines;
obtaining a plurality of first front images of the fundus at different times using return light from the fundus in the first field, and obtaining a plurality of second front images of the fundus at different times using the return light from the fundus in the second field; and
in a case where at least one of the first front images is selected as a reference image, detecting movement of the subject's eye using information indicating a position gap between the reference image and the first front images, and in a case where at least one of the second front images is selected as the reference image, detecting the movement of the subject's eye using information indicating a position gap between the reference image and the second front images.

13. A non-transitory computer-readable storage medium storing a program for causing a computer to execute the method according to claim 11.

14. A non-transitory computer-readable storage medium storing a program for causing a computer to execute the method according to claim 12.

15. An ophthalmic apparatus comprising:
a scanning unit configured to scan a fundus of a subject's eye with illumination light;
a control unit configured to control the scanning unit to two-dimensionally scan a first field of the fundus with the illumination light and two-dimensionally scan a second field different from the first field with the illumination light so that scanning lines of the first field and scanning lines of the second field are alternately arranged in a direction crossing the scanning lines;
a front image acquisition unit configured to obtain first front images of the fundus at different times using return light from the fundus in the first field, and obtain second front images of the fundus at different times using return light from the fundus in the second field; and
a detection unit configured to, in a case where at least one of the first front images is selected as a reference image, detect a movement of the subject's eye using information indicating a position gap between the reference image and the second front images and information indicating a difference in position between the first field and the second field.

16. The ophthalmic apparatus according to claim 15,
wherein the first field is either one of an odd number field in which odd-numbered lines scanned in odd-numbered turns are obtained and an even number field in which even-numbered lines scanned in even-numbered turns are obtained, and
wherein the second field is the other field of said either one.

17. The ophthalmic apparatus according to claim 15, wherein the control unit is configured to control the scanning unit so that a forward scan of the first field and a backward scan of the second field cross each other, and a backward scan of the first field and a forward scan of the second field cross each other.

18. The ophthalmic apparatus according to claim 17, wherein the scanning unit includes a main scanning unit configured to scan the fundus with the illumination light by forward and backward scans in a main scanning direction, and a sub scanning unit configured to scan the fundus with the illumination light at substantially constant speed.

19. The ophthalmic apparatus according to claim 15, further comprising:
an OCT scanning unit configured to scan the fundus with measurement light; and
a tomographic image acquisition unit configured to obtain a tomographic image of the fundus by using light obtained by combining return light from the fundus irradiated with the measurement light and reference light corresponding to the measurement light,
wherein the control unit is configured to control the OCT scanning unit using information indicating the detected movement.

20. The ophthalmic apparatus according to claim 15, wherein the detection unit is configured to obtain information indicating the position gap between the reference image and the first front images by performing two-dimensional correlation calculation between the reference image and the first front images, and obtain information indicating the position gap between the reference image and the second front images by performing two-dimensional correlation calculation between the reference image and the second front images.

21. The ophthalmic apparatus according to claim 20, wherein the detection unit is configured to perform the two-dimensional correlation calculation in units of subpixels.

* * * * *